United States Patent
Cherkas et al.

(10) Patent No.: US 9,795,512 B2
(45) Date of Patent: Oct. 24, 2017

(54) MEASURING MODULE INCLUDING AN INTERFACE FOR COUPLING TO A LASER DEVICE

(71) Applicant: Novartis AG, Basel (CH)

(72) Inventors: Nadzeya Cherkas, Darmstadt (DE); Irina Kadetov, Röthenbach an der Pegnitz (DE); Olaf Kittelmann, Berlin (DE); Klaus Vogler, Eckental (DE)

(73) Assignee: Novartis AG (CH)

( * ) Notice: Subject to any disclaimer, the term of this patent is extended or adjusted under 35 U.S.C. 154(b) by 57 days.

(21) Appl. No.: 14/422,648

(22) PCT Filed: May 23, 2014

(86) PCT No.: PCT/EP2014/060675
§ 371 (c)(1),
(2) Date: Feb. 19, 2015

(87) PCT Pub. No.: WO2015/176773
PCT Pub. Date: Nov. 26, 2015

(65) Prior Publication Data
US 2015/0335478 A1 Nov. 26, 2015

(51) Int. Cl.
*A61B 18/18* (2006.01)
*A61F 9/009* (2006.01)
(Continued)

(52) U.S. Cl.
CPC ............ *A61F 9/009* (2013.01); *A61F 9/008* (2013.01); *A61F 9/00825* (2013.01); *G01T 1/24* (2013.01);
(Continued)

(58) Field of Classification Search
CPC ............ A61F 2009/00872; A61F 9/008; A61F 9/00804
(Continued)

(56) References Cited

U.S. PATENT DOCUMENTS

2005/0241653 A1* 11/2005 Van Heugten .......... A61F 9/007
128/898
2008/0165405 A1* 7/2008 Bruestle ............... B23K 26/046
359/223.1

(Continued)

FOREIGN PATENT DOCUMENTS

EP 1279385 A1 1/2003
WO 2014075713 A1 5/2014

*Primary Examiner* — Daniel Cerioni
(74) *Attorney, Agent, or Firm* — Keiko Ichiye

(57) ABSTRACT

An apparatus for laser-assisted eye treatment comprises a laser device and first and second accessory modules. The laser device is configured to provide focused laser radiation and has a coupling port. The first accessory module may form a patient interface and has a contact surface for an eye. The second accessory module includes a measuring device that performs measurements of the laser radiation. In certain embodiments, the measurements include the measurement of a pulse duration of the laser radiation using a detector operating on the basis of two-photon absorption. The first and second accessory modules are configured to detachably couple to the laser device at the coupling port. Only one accessory module can be coupled to the coupling port at a time. Therefore, the first accessory module must be removed from the coupling port before the second accessory module can be attached to the coupling port.

6 Claims, 3 Drawing Sheets

(51) Int. Cl.
*G01T 1/24* (2006.01)
*A61F 9/008* (2006.01)

(52) U.S. Cl.
CPC ..... *A61F 9/0084* (2013.01); *A61F 2009/0087* (2013.01); *A61F 2009/00872* (2013.01)

(58) Field of Classification Search
USPC .......................................................... 606/5
See application file for complete search history.

(56) References Cited

U.S. PATENT DOCUMENTS

| | | | |
|---|---|---|---|
| 2013/0165911 A1 | 6/2013 | Raksi et al. | |
| 2014/0128856 A1* | 5/2014 | Wysopal | A61F 9/00825 606/5 |
| 2014/0228825 A1* | 8/2014 | Gorschboth | A61F 9/008 606/5 |
| 2014/0361145 A1* | 12/2014 | Vogler | A61F 9/008 250/201.1 |
| 2015/0025510 A1* | 1/2015 | Vogler | A61F 9/00825 606/4 |

* cited by examiner

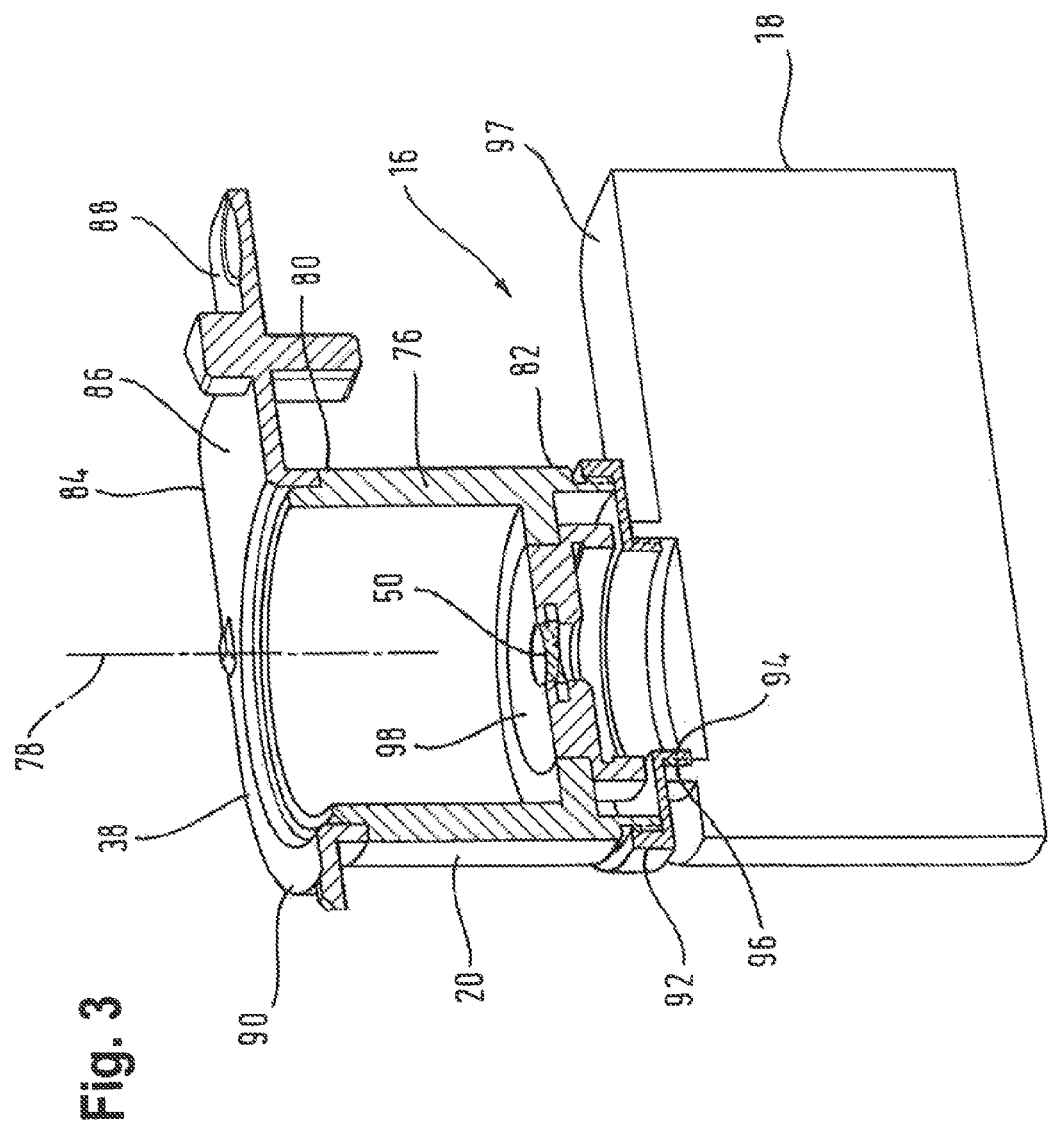

MEASURING MODULE INCLUDING AN INTERFACE FOR COUPLING TO A LASER DEVICE

CROSS REFERENCE TO RELATED APPLICATIONS

This application is a section 371 national stage phase of International Application No. PCT/EP2014/060675, filed 23 May 2014, titled "MEASURING MODULE INCLUDING AN INTERFACE FOR COUPLING TO A LASER DEVICE," which is hereby incorporated by reference in its entirety.

The present disclosure pertains to an apparatus for laser assisted treatment. More specifically, the present disclosure pertains to a measuring module permitting measurements of radiation emitted by a laser device, and a manner of mounting such measuring module to the laser device. In certain embodiments, measuring values determined by the measuring module are used to determine information on a pulse duration of the radiation emitted by the laser device.

Laser devices providing pulsed laser radiation of ultra short pulse duration have found their way into an array of applications including e.g., the field of laser assisted treatment. Within the context of this disclosure, an ultra short pulse duration is intended to refer to a pulse duration in the attosecond, picosecond, femtosecond or nanosecond range.

In the field of laser assisted treatment of a human eye, ultra short-pulsed laser radiation is frequently used for the purpose of generating one or more incisions in eye tissue.

In the conventional art, a laser device used for the generation of incisions in human eye tissue is sometimes deployed together with an accessory module equipped with a contact member that is transmissive for the laser radiation of the laser device and provides a contact surface for the eye to be treated. This accessory module is frequently referred to as a patient interface. Typically, it is a single use item which is disposed after a single use. In view of the need for disposability, provisions must be made to couple the patient interface to the laser device in a detachable manner. For this, the laser device may provide an appropriate coupling port.

An exemplary embodiment of a patient interface in the conventional art is described and shown in WO 2012/041347 A1, the entire content of which is incorporated herein by reference.

Where a laser device is deployed for the treatment of an eye (or for any other type of application), it should be ensured that the laser radiation emitted by the laser device complies with specific, pre-defined requirements. One radiation parameter that is determinative for the quality of the radiation and thus the quality and success of the treatment is the duration of the individual radiation pulses of the laser radiation. It is not only desirable to be able to measure the pulse duration during production of the laser device in order to configure the laser device appropriately, but also to be able to examine the pulse duration from time to time after delivery of the laser device to the customer in order to ascertain potential deviations from one or more nominal values. Such deviations can be due to aging of the laser devise or may be caused by changing environmental conditions of the laser device, e.g., changes in the ambient temperature or the humidity of the air. It would be inefficient if a service man of the manufacturer would have to be called whenever it is wished to check the pulse duration at the site of deployment of the laser device. It would be preferable if the requisite measurements or tests can be performed from time to time by the customer/user himself. For this, it is desirable to provide the user with easy-to-handle equipment that can be mounted to the laser device on demand in order to perform measurements of the laser radiation of the laser device. It is particularly desirable that no structural modifications need to be made on the laser device in order to mount a measuring equipment and that no need should exist to transfer the laser device from its normal place of use to a remote, dedicated measuring station.

For this purpose, the present disclosure provides an apparatus for laser assisted eye treatment, comprising: a laser device configured to provide focused laser radiation and having a coupling port; a first accessory module having a contact surface for an eye and configured to detachably couple to the laser device at the coupling port; and a second accessory module including a measuring device that performs measurements of the laser radiation, the second accessory module being configured to detachably couple to the laser device at the coupling port in place of the first accessory module.

The apparatus allows to utilize one and the same coupling port of the laser device for selectively mounting the first accessory module (which may include, or form, a patient interface of the type described further above) or the second accessory module to the laser device. The use of the second accessory module then requires that the coupling port is free and a previously attached patient interface has been removed. The second accessory module (which may be referred to as a measuring module) requires substantially the same effort for attachment and detachment as the first accessory module. Considering that laser devices are commercially available which provide an easy-to-use coupling port for the coupling of a patient interface, the present invention permits a similarly easy employment of a measuring module with such laser devices, wherein the measuring module can be designed for everyday use.

Within the scope of the present disclosure, the coupling port encompasses any structure(s) contributing on the side of the laser device to the coupling of the first and second accessory modules. For example, the coupling port may include one or more coupling elements ensuring at least one of a form-fit, a force-fit and a magnetic-force engagement with the first or second accessory module. A force-fit connection may be realized e.g., by a screw or a clamp. For a force-fit connection, the coupling port may provide a slide-in structure allowing for sliding insertion of the first or second accessory module in a direction transverse to the direction of propagation of the radiation. When inserted into the slide-in structure, the first or second accessory module is positionally secured in the direction of propagation of the radiation by a form fit. One or more stop surfaces associated with the slide-in structure may also ensure a positional form-fit fixation of the first or second accessory module in the direction of insertion.

The coupling port may comprise at least one coupling structure commonly used by the first accessory module and the second accessory module. In addition, the coupling port may comprise at least one other coupling structure exclusively used by one of the accessory modules. Thus, the present disclosure provides for the possibility that a portion of the coupling port is used by one of the first and second accessory modules, but not by the other. In other embodiments, the entirety of the coupling port is used by both the first accessory module and the second accessory module.

According to embodiments, the coupling port may include a slide-in structure adapted to slidingly receive a selected one of the first and second accessory modules. The slide-in structure may include at least one slot, and the first accessory module and the second accessory module may each include at least one rim portion for sliding insertion into the slot.

A patient interface as disclosed in WO 2012/041347 A1 is a possible embodiment of the first accessory module. While this document discloses a one-piece, i.e. integral, configuration of the patient interface, it is to be understood that this is in no way intended to be limiting to the present disclosure. A multi-part configuration of the patient interface is equally conceivable within the scope of the present disclosure. In certain embodiments, the second accessory module includes at least one measuring sensor and one or more lenses disposed upstream of the measuring sensor in a propagation direction of the laser radiation, the one or more lenses adapted to change, or shape, a divergence of the laser radiation. In some embodiments, the one or more lenses may be adapted to collimate the laser radiation. Laser devices using ultra short-pulsed laser radiation for cutting into human eye tissue are typically characterized by a comparatively large numerical aperture of the (focused) laser beam delivered by the laser device. In other words, the divergence of the beam as it leaves the laser device is comparatively large. Under such circumstances it may be advantageous to collimate (i.e. make parallel or substantially parallel) the focused laser beam to achieve a radiation intensity that is as high as possible at the site of the measuring sensor. The one or more lenses used for changing or shaping the divergence of the laser radiation may consist of a single lens, in certain embodiments. In other embodiments, a multi-lens configuration of the one or more lenses is conceivable. In certain embodiments, the one or more lenses are disposed upstream of a focus of the laser radiation in the propagation direction thereof and have a diverging characteristic. It is to be understood, however, that embodiments wherein the one or more lenses are disposed downstream of the focus in the propagation direction of the laser radiation are also intended to be within the scope of the present disclosure. In such embodiments, the one or more lenses will have a converging characteristic for the laser radiation.

According to certain embodiments, the second accessory module may include a plurality of sections releasably connected to each other, wherein a first section among the plurality of sections accommodates the one or more lenses and a second section among the plurality of sections accommodates the at least one measuring sensor, and wherein the first section includes a coupling structure to engage with the coupling port of the laser device. A configuration of the second accessory module with a plurality of sections opens the possibility to resort to a commercially available measuring device and design a suitable interface, so that the interface is matched to the coupling port of the laser device and is adapted for connection with the measuring device. The connection of the first and second sections of the second accessory module may be, e.g., through threading engagement.

In certain embodiments, the measuring device is configured to measure a radiation intensity of the laser radiation and determine a pulse duration of the laser radiation on the basis of the measured radiation intensity. For this, the measuring device may include a first photodetector operating on the basis of two-photon absorption. The first photodetector may output a detector signal which—as is generally known from the theory of two-photon absorption—may be proportional to the square of the radiation intensity incident at the detection surface of the first photodetector. Further, the incident intensity is proportional to the pulse peak power for constant geometrical irradiation conditions, and the pulse peak power is inversely proportional to the pulse duration for a given pulse energy and a given pulse repetition rate, i.e. for a given average power. The above relationship can be expressed mathematically as follows:

$$\hat{P} = \frac{E_p}{\tau} = \frac{\overline{P}}{\tau \cdot f}$$

In the above equation, $\hat{P}$ designates the pulse peak power, $E_p$ designates the pulse energy, $\tau$ designates the pulse duration, $\overline{P}$ designates the average power of the laser device and f designates the pulse repetition rate. Accordingly, the pulse duration can be determined on the basis of the measured pulse peak power. Further, it is possible to detect an occurrence of undesired double pulses based on an analysis of the determined pulse duration. Such double pulses may, e.g., be an indication for malfunctions of a mode-locking operation of the laser device.

In certain embodiments, the measuring device includes a second photodetector operating on the basis of one-photon absorption. The second photodetector thus allows to obtain a measurement of the average laser power of the laser device.

The present disclosure further provides a method for operating a laser device adapted to provide focused laser radiation, the laser device including a coupling port, wherein the method comprises steps of: removing from the laser device a first accessory module detachably coupled to the laser device at the coupling port, the first accessory module including a contact surface for an eye, wherein the removing includes mechanically disengaging a coupling structure of the coupling port from a complementary coupling structure of the first accessory module; subsequent to the removing of the first accessory module, coupling a second accessory module to the laser device at the coupling port, the second accessory module including a measuring device, wherein the coupling includes mechanically engaging the coupling structure of the coupling port with a complimentary coupling structure of the second accessory module; and while the second accessory module is in a state of being coupled to the laser device, operating the measuring device for performing measurements on the laser radiation.

Certain embodiments of the present invention will become more apparent from the following description of the accompanying drawings, in which:

FIG. 3 is a partially broken-away view showing details of the measuring module of FIG. 1, according to an embodiment.

Figure 1:
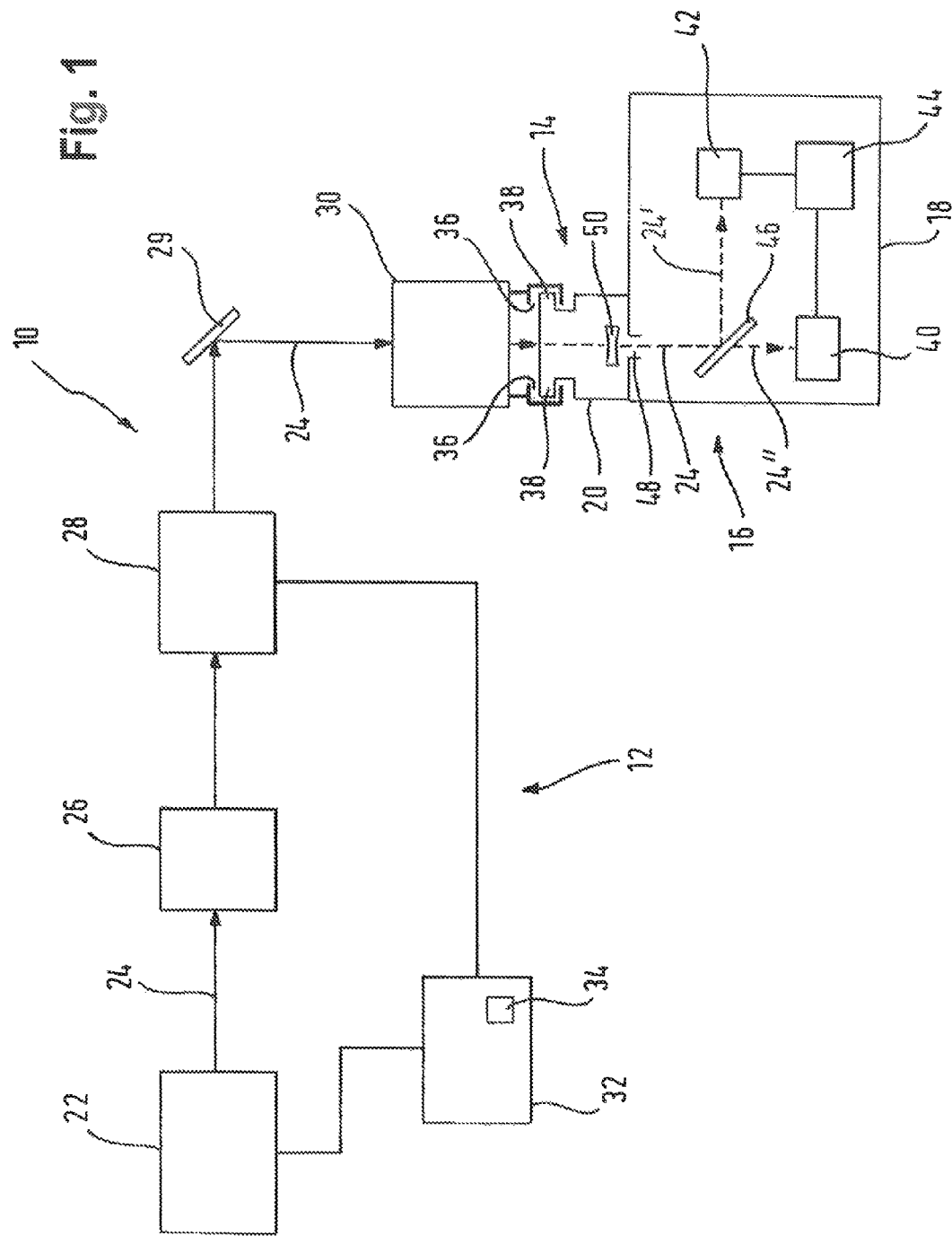
FIG. 1 shows a schematic diagram of an ophthalmic laser apparatus according to an embodiment in a first configuration in which a measuring module is attached to a focusing objective of a laser device.

Reference is initially made to FIG. 1. This Figure depicts in a highly schematic manner a laser apparatus 10 which is designed for use in laser-assisted ophthalmic procedures. More specifically, the laser apparatus 10 is designed for creating incisions in human eye tissue using ultra short-pulsed laser radiation, wherein the radiation may have a center wavelength in an infrared range (such as, e.g., between ca. 800 nm and ca. 1300 nm) or in an ultraviolet range above ca. 300 nm, wherein the limit of ca. 300 nm is intended to ensure sufficient transmission of the radiation into or through the cornea of an eye to be treated. An exemplary UV range which may be useful for creating incisions in the eye is from ca. 340 nm to 360 nm.

The laser apparatus 10 includes a laser device 12 as well as a plurality of accessory modules which may be coupled with the laser device 12, each at a time. These accessory modules include different types of accessory modules wherein each type is designed for a different purpose and functionality. The laser device 12 has a coupling port 14 which is commonly used by all accessory modules. Accordingly, whenever a user (e.g., a physician or assistant) of the laser apparatus 10 wants to use a first type of accessory module with the laser device 12 and subsequently a second type of accessory module, he or she must remove the first type of accessory module from the coupling port 14 before he or she can attach the second type of accessory module at the coupling port 14.

Figure 2:
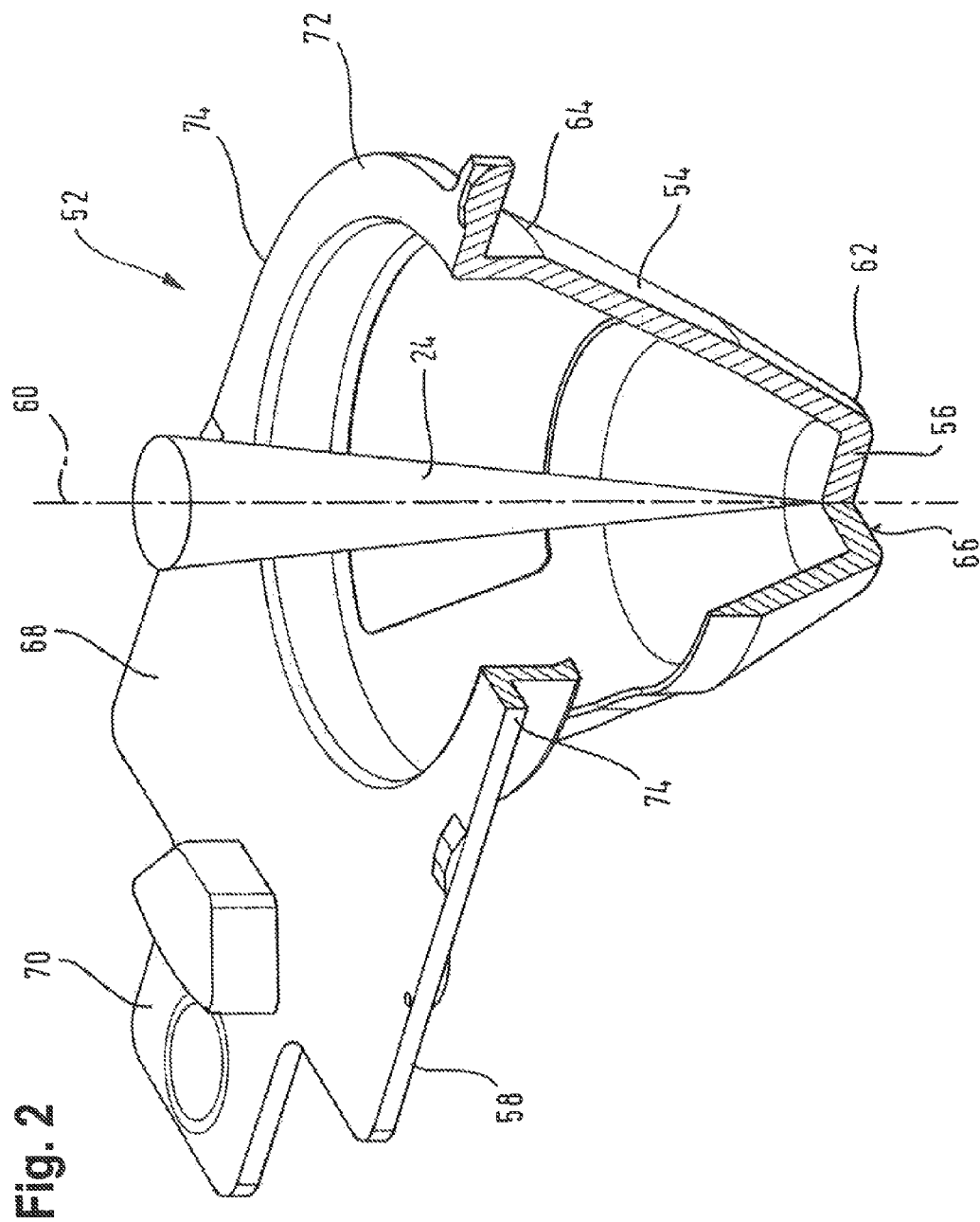
FIG. 2 illustrates a perspective, partially broken-away view of a patient interface according to an embodiment, wherein the patient interface can be attached to the focusing objective of the laser device of FIG. 1 in place of the measuring module.

The different types of accessory module include, in certain embodiments, a measuring module 16 (also shown in FIG. 3) and a patient interface (shown in FIG. 2). The measuring module 16 allows measurements of the laser radiation to be made at the installation site of the laser device 12. More particularly, the measuring module 16 is configured to determine a pulse peak power of the laser radiation based on the effect of two-photon absorption. As will be generally understood by one versed in the art, two-photon absorption refers to the process of a molecule transitioning from a ground state to an excited state when the molecule absorbs two photons simultaneously. By using a TPA (two-photon absorption) detector having a suitably selected band gap between the ground state and the excited state, it can be ensured that for a given wavelength of the laser radiation the TPA detector will only output a detector signal in the case of a TPA event.

Compared with one-photon absorption wherein a single photon suffices to cause a molecule to transition to an excited state, the probability of TPA events is substantially lower. In general, the number of TPA events, and thus the signal magnitude of a TPA detector, has a quadratic dependency of the incident intensity of the laser radiation, whereas the detector signal of a SPA (single-photon-, or one-photon-absorption) will show a linear dependency of the incident intensity. For a given detector and for given radiation parameters of the laser radiation, the intensity is proportional to the pulse peak power, and for a given pulse energy and a given pulse repetition rate, i.e. for a given average power of the laser radiation, the pulse peak power is inversely proportional to the pulse duration. It is thus possible to determine the pulse duration from the signal strength of a TPA detector, e.g., when related to the signal strength of the SPA detector.

In the exemplary embodiment of FIG. 1, the measuring module 16 includes a plurality of sections (or sub-modules) which are detachably connected with each other. More specifically, the measuring module 16 includes a detector section 18 and an interface section 20. For example, the detector section 18 and the interface section 20 are threadingly connected with each other. Thus, the detector section 18 may be provided with one or more threaded structures (not shown in FIG. 1) and the interface section 20 may be provided with one or more complementary threaded structures (equally not shown in FIG. 1), so that the detector section 18 and the interface section 20 can be connected with, and disconnected from, each other by way of e.g., sliding or screwing action. It is to be understood that the present disclosure is not limited to a screw or slide connection between the detector section 18 and the interface section 20 and that various other types of releasable connection can be envisaged, e.g., a bayonet connection.

In certain embodiments, the detector section 18 is, or includes, a commercially available detector device such as, e.g., a peak power detector. The interface section 20 may be viewed as forming a matching tool allowing matching of the detector section 18 to the laser device 12 mechanically and/or optically. Depending on the particular design of the detector section 18, the interface section 20 may take different configurations.

The laser device 12 includes a laser source 22 generating a laser beam 24. A beam expander 26 serves to expand the laser beam 24. Following beam expansion by the beam expander 26, the laser beam 24 enters a scanning device 28 where the beam 24 is subjected to x-y scanning, i.e. scanning in a direction orthogonal to a propagation direction of the beam 24. For example, the scanning device 28 may include, in a manner generally know per se in the art, a pair of scanning mirrors, e.g., a pair of galvanometrically actuated scanner mirrors, supported to tilt about mutually orthogonal tilt axes or an electro-optical crystal that can electro-optically steer the laser beam. A focusing objective 30 disposed downstream (i.e. with respect to the propagation direction of the beam 24) of the scanning device 28 serves to focus the laser beam 24 to a focal point. The focusing objective 30 may, for example, be of a F-θ type or may be any other type.

A control unit 32 is provided for controlling the operation of the laser source 22 and the scanning device 28 under control of a control program schematically represented at 34 in FIG. 1. The control program 34 may include program instructions designed to bring about one or more incisions in eye tissue of a patient undergoing an eye surgical procedure. For example, an incision may be made in corneal tissue as part of a LASIK (laser in-situ keratomileusis) treatment in order to prepare a corneal flap, which is a disc of tissue that remains connected with surrounding corneal tissue, so that it can be folded aside and, following an ablating laser treatment of stromal tissue disposed underneath the flap, can be folded back to cover the treatment site. Other types of treatment requiring the generation of one or more corneal incisions include corneal lenticule extraction and keratoplasty (lamellar or penetrating). Other tissue portions of a human eye may equally require the generation of one or more incisions in the course of a surgical treatment. For example, a cataract surgery may require the generation of one or more incisions in the human lens.

It is needless to say that the present disclosure is in no way intended to be limited to specific types of treatment and that the above-mentioned types of treatment are only given by way of example. In addition, the present invention is also applicable in view of making incisions or cuts in work pieces, i.e. when processing a non-biological material.

The laser device 12 may further be equipped with z-scanning capability for the focal point of the laser beam 24, i.e. with capability for shifting the focal point along the propagation direction of the beam 24. The z-scanning capability may be implemented in the scanning device 28 or in the beam expander 26 and may, e.g., be effected by means of a controllable optical element of variable position or variable refractive power. In a case where the z-scanning capability is implemented in the beam expander 26, the control unit 32 will also have a control connection with the beam expander 26. For example, the scanning device 28 may include a longitudinally adjustable lens, a lens of electrically variable refractive power, or a deformable mirror 29 that can control the z-position of the beam focus.

The coupling port 14 is formed at an output side of the focusing objective 30, i.e. at a side of the focusing objective 30 where the laser beam 24 leaves the objective 30. More specifically, the coupling port 14 includes one or more coupling structures connected with, or formed on, a casing (not shown in detail in FIG. 1) accommodating the optical system of the focusing objective 30. In the exemplary embodiment shown in FIG. 1, the coupling port 14 includes a pair of coupling slots 36 arranged at a distance from each other and having open slot sides facing each other. The slots 36 define a slide-in structure allowing for sliding insertion of the interface section 20 with a sliding motion parallel to an x-y plane. Here, the x-y plane refers to a plane orthogonal to the propagation direction of the laser beam 24 as it leaves the focusing objective 30. As shown in FIG. 1, the interface section 20 comprises rib-like rim portions (or flange portions) 38 serving as coupling structures of the interface section 20 for engaging into the coupling slots 36. Attachment of the interface section 20 the laser device 12 is thus effected by inserting the rim portions 38 into the coupling slots 36 and pushing the interface section 20 from an insertion-start position to an insertion-end position along an x-y plane wherein the insertion-end position may be defined by one or more stop surfaces (not shown in the drawings) provided by the coupling port 14 in association with each coupling slot 36.

The coupling slots 36 and the rim portions 38 are suitable sized and shaped so as to ensure a sufficiently tight fit of the rim portions 38 in the coupling slots 36 in the direction of propagation of laser beam 24, to thereby avoid undesired movement play of the interface section 20 with respect to the focusing objective 30 in the beam propagation direction.

In the exemplary embodiments, the detector section 18 includes a TPA detector 40, a SPA detector 42, an evaluation unit 44, and a beam splitter 46. After leaving the focusing objective 30 and travelling through the interface section 20, the laser beam 24 enters the detector section 18 where it is divided by the beam splitter 46 (e.g., a semi-transparent mirror) into a first partial beam 24' and a second partial beam 24". The first partial beam 24' is directed onto the SPA detector 42, which operates on the basis of one-photon absorption and delivers a detector signal that is representative of the average power of the first partial beam 24' and thus the laser beam 24. The second partial beam 24" is directed onto the TPA detector 40, which delivers a detector signal that is representative of the peak pulse power of the second partial beam 24' and hence the laser beam 24. The evaluation unit 44 receives the detector signals produced by the detectors 40, 42 and determines the pulse duration of the laser beam 24 based on the detector signals. In alternate embodiments, the control unit 32 may be configured to receive and process the detector signals from the detectors 40, 42 and calculate the pulse duration.

It is desirable for the laser beam 24 to be collimated as it enters the detector section 18. The detector section 18 may have an entrance window or opening 48 (schematically depicted in FIG. 1) of a given size through which the laser beam 24 enters the detector section 18. To ensure that the laser beam 24 is a collimated beam as it enters the detector section 18 through the entrance window or opening 48, the interface section 20 accommodates a lens 50 that is effective to cause the desired collimation of the laser beam 24. In the exemplary embodiment shown in FIG. 1, the lens 50 is configured as a diverging lens, which can achieve the desired collimation if the focal point of the laser beam 24 leaving the focusing objective 30 is located downstream of the lens 50 in the beam propagation direction. In alternate embodiments, the focusing objective 30 may focus the laser beam 24 to a point located upstream of the lens 50, in which case the lens 50 will be configured as a converging lens. It is to be understood that although FIG. 1 shows the lens 50 as a single lens, a system of (two or more) lenses may be provided for the collimation of the laser beam 24 instead.

Additional reference is now made to FIG. 2, which shows a patient interface 52 having a body portion 54, a contact member 56 and a gripping and coupling section 58. The body portion 54 is formed, in the exemplary embodiment of FIG. 2, as a substantially conical, sleeve-like member having an axis 60, a narrower axial end portion 62 and a wider axial end portion 64. When installed on the laser device 12 of FIG. 1, i.e. when coupled to the coupling port 14, the patient interface 52 has its axis 60 oriented in the direction of beam propagation. For illustrative purposes, FIG. 2 shows the focused laser beam 24 as delivered from the focusing objective 30.

The contact member 56 is disposed in the region of the narrower axial end portion 62 of the body portion 54 and provides a contact surface 66 for abutment by the eye to be treated. While in the exemplary embodiment FIG. 2 the contact member 56 is formed as an applanation plate having parallel main surfaces, it is to be understood that the contact member 56 may in alternate embodiments have a different surface design. For example, the contact surface 66 may be formed with a concave shape or a convex shape or any other non-planar shape. The material of at least of the contact member 56 is transmissive for the laser radiation of the beam 24 so that the radiation can penetrate into the tissue of an eye resting against the contact surface 66.

The gripping and coupling section 58 comprises a plate member 68 connected with the body portion 54 in the region of the wider axial end portion 64 of the body portion 54 and oriented to extend in a plane orthogonal to the axis 60. The plate member 68 provides a gripping projection 70 allowing a user of the laser apparatus 10 to grip the patient interface 52 without contaminating critical parts of the patient interface 52 such as the contact member 56. The plate member 68 transitions into a radially (with respect to the axis 60) projecting flange 72 extending along at least a part of the periphery of the body portion 54. The flange 72 forms rim portions 74 designed to engage into the coupling slots 36 of the coupling port 14 when the patient port 52 is mounted to the laser device 12. The rim portions 74 are intended to correspond in function and design to the rim portions 38 of FIG. 1.

FIG. 3 shows details of an exemplary embodiment of the measuring module 16 of FIG. 1. As can be seen, the interface section 20 comprises a cylindrical interface body 76 having an axis 78 and first and second axial end portions 80, 82. In the region of the first axial end portion 80, a gripping and coupling section 84 is connected with the interface body 76. The gripping and coupling section 84 is of corresponding design to that of the gripping and coupling section 58 of the patient interface 52. More specifically, the gripping and coupling section 84 of the interface section 20 comprises a plate member 86 providing a gripping projection 88, wherein the plate member 86 and the gripping projection 88 are functionally and structurally similar or identical to the plate member 68 and the gripping projection 70 of the patient interface 52. Further, the gripping and coupling section 84 comprises a radially projecting flange 90 which is similar or identical in function and structure to the flange 72 of the patient interface 52 and forms the rim portions 38 shown in FIG. 1. In FIG. 3, only one of the rim portions 38 can be seen owing to the broken-away illustration of the interface section 20.

In the region of its second axial end portion 82, the interface body 76 is fitted with a retaining ring 92 having a threaded ring portion 94 in threading engagement with an annular threaded portion 96 of a housing 97 of the detector section 18. The retainer ring 92 thus allows to connect the interface section 20 and the detector section 18 by screwing together the threaded portions 94, 96 and allows to decouple the interface section 20 and the detector section 18 by unscrewing the threaded portions 94, 96.

The lens 50 is supported inside of the interface body 76 by means of a support member 98, which in the illustrated exemplary embodiment is a separate member from the interface body 76 and is replaceably and/or adjustably connected to the interface body 76. A separate configuration of the interface body 76 and the support member 98 is useful for the purpose of identifying a suitable axial position for the lens 50 through tests made with different sizes of the support member 98 and/or at different relative axial positions of the support member 98 and the interface body 76. For example, the connection between the support member 98 and the interface body 76 may be a screwing connection, whereby the axial position of the support member 98 and thus the lens 50 with respect to the interface body 76 can be adjusted by rotation of the support member 98 about the axis 78. In alternate embodiments, the support member 98 is integrally formed with the interface body 76.

The invention claimed is:

1. An apparatus for laser assisted eye treatment, comprising:
 a laser device configured to provide focused laser radiation for eye treatment, the laser device comprising:
  a focusing objective that focuses the laser radiation; and
  a coupling port;
 a first accessory module having a contact surface for an eye to be treated and configured to detachably couple to the laser device at the coupling port, the contact surface receives the laser radiation from the focusing objective when the first accessory module is coupled to the laser device; and
 a second accessory module configured to detachably couple to the laser device at the coupling port in place of the first accessory module, the second accessory module including a plurality of sections releasably connected to each other, the sections comprising:
 a detector section comprising:
  one or more photodetectors that each detect at least a portion of the laser radiation and generate a detector signal; and
  an evaluation unit that determines a pulse duration of the laser radiation based on the one or more detector signals; and
 an interface section that receives the laser radiation from the focusing objective when the second accessory module is coupled to the laser device, the interface section comprising:
  a cylindrical interface body having an axis;
  a coupling structure that can engage with the coupling port of the laser device; and
  a lens disposed along the axis and distinct from the focusing objective of the laser device, the lens operates to:
   collimate the laser radiation from the focusing objective; and
   send the collimated laser radiation along the axis directly to the detector section.

2. Apparatus of claim 1, wherein the coupling port includes a slide-in structure adapted to slidingly receive a selected one of the first and second accessory modules.

3. Apparatus of claim 2, wherein the slide-in structure includes at least one slot, wherein the first accessory module and the second accessory module each include at least one rim portion for sliding insertion into the slot.

4. Laser apparatus of claim 1, wherein the first and second sections are threadingly connected to each other.

5. Apparatus of claim 1, wherein the one or more photodetectors include a first photodetector operating on the basis of two-photon absorption.

6. Apparatus of claim 1, wherein the one or more photodetectors include a second photodetector operating on the basis of one-photon absorption.

* * * * *